(12) United States Patent
Ritter et al.

(10) Patent No.: US 7,698,098 B2
(45) Date of Patent: Apr. 13, 2010

(54) EFFICIENT SPECTRAL MATCHING, PARTICULARLY FOR MULTICOMPONENT SPECTRA

(75) Inventors: Gary L. Ritter, Madison, WI (US); William J. McCarthy, Madison, WI (US); Kathleen A. Larson, Madison, WI (US); Alexander I. Grenov, Madison, WI (US); Federico Izzia, Madison, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 269 days.

(21) Appl. No.: 12/032,794

(22) Filed: Feb. 18, 2008

(65) Prior Publication Data
US 2009/0210194 A1    Aug. 20, 2009

(51) Int. Cl.
*G06F 15/00* (2006.01)

(52) U.S. Cl. .................. 702/179; 702/189; 250/282; 250/307; 250/310; 356/402

(58) Field of Classification Search ............. 702/27–32, 702/179, 189, 194, 134, 137, 181, 40; 250/306, 250/307, 310, 311, 282, 347, 461.2, 339.05, 250/339.07, 339.12, 349, 353; 356/328, 356/303, 307, 326, 301, 456, 402

See application file for complete search history.

(56) References Cited

U.S. PATENT DOCUMENTS

| | | | |
|---|---|---|---|
| 5,347,460 A | | 9/1994 | Gifford et al. |
| 5,538,897 A | * | 7/1996 | Yates et al. ............. 436/89 |
| 5,668,373 A | | 9/1997 | Robbat, Jr. et al. |
| 6,075,594 A | | 6/2000 | Thomas et al. |
| 6,140,643 A | * | 10/2000 | Brown et al. ............. 850/10 |
| 6,728,663 B2 | | 4/2004 | Krukar et al. |
| 6,745,133 B2 | | 6/2004 | Axelsson |

(Continued)

FOREIGN PATENT DOCUMENTS

JP    60098335 A    *    6/1985

(Continued)

OTHER PUBLICATIONS

Chi-Shi Chen et al., "Searching a Mid-Infrared Spectral Library of Solids and Liquids with Spectra of Mixtures," Vibrational Spectroscopy, vol. 14, No. 1, pp. 9-17, (1997).

(Continued)

*Primary Examiner*—Carol S Tsai
(74) *Attorney, Agent, or Firm*—DeWitt Ross & Stevens; Michael C. Staggs (57) ABSTRACT

An unknown spectrum obtained from infrared or other spectroscopy can be compared to spectra in a reference library to find the best matches. The best match spectra can then each in turn be combined with the reference spectra, with the combinations also being screened for best matches versus the unknown spectrum. These resulting best matches can then also undergo the foregoing combination and comparison steps. The process can repeat in this manner until an appropriate stopping point is reached, for example, when a desired number of best matches are identified, when some predetermined number of iterations has been performed, etc. This methodology is able to return best-match spectra (and combinations of spectra) with far fewer computational steps and greater speed than if all possible combinations of reference spectra are considered.

25 Claims, 4 Drawing Sheets

U.S. PATENT DOCUMENTS

| | | | |
|---|---|---|---|
| 6,906,320 B2 | 6/2005 | Sachs et al. | |
| 7,049,581 B2* | 5/2006 | Whitney et al. | 250/282 |
| 7,072,770 B1 | 7/2006 | Schweitzer et al. | |
| 7,219,038 B2 | 5/2007 | Tracy et al. | |
| 7,230,233 B2* | 6/2007 | Whitney et al. | 250/282 |
| 7,257,148 B2* | 8/2007 | Suzuki | 375/146 |
| 7,471,716 B2* | 12/2008 | Tamaki | 375/150 |
| 2005/0006576 A1* | 1/2005 | Whitney et al. | 250/281 |
| 2006/0219894 A1* | 10/2006 | Whitney et al. | 250/288 |
| 2007/0090285 A1* | 4/2007 | Whitney et al. | 250/281 |
| 2008/0067344 A1* | 3/2008 | Yamaguchi et al. | 250/282 |

FOREIGN PATENT DOCUMENTS

| | | | |
|---|---|---|---|
| JP | 2002202259 A | * | 7/2002 |
| JP | 2005083952 A | * | 3/2005 |

OTHER PUBLICATIONS

M. R. Nyden, "Computer-Assisted Spectroscopic Analysis Using Orthonormalized Reference Spectra. I. Application to Mixtures," Australasian Physical and Engineering Sciences in Medicine, Medicine, Melbourne, vol. 40, No. 6, pp. 868-871, (1986).

* cited by examiner

| Spectrum Name: | | Film Sample | | | |
|---|---|---|---|---|---|
| Spectrum File: | | C:\MyDocuments\testresults\spectra\absorb.spa | | | |
| Spectrum Date: | | Fri Feb 15 2008 11:13:08 (CST) | | | |
| Rank / Index | Match Value | Source Index | Compound Name | Source of Compound | Cumulative Match | Weight |
| 1 | 99.58 | 2 | Polystyrene Film | User Library | 99.58 | 5.4195 |
| 2 | 68.97 | 10 | Toluene (Transmission Cell) | FTIRSearch.com | 56.96 | 5.7799 |
| | | 22 | ABS Plastic (ATR Corrected) | NIST Library | 68.92 | 29.3250 |
| | | 3 | Polytetrafluoroethylene Film | C:\MyDocuments\reference | 68.97 | 30.3022 |
| 3 | 68.93 | 10 | Toluene (Transmission Cell) | FTIRSearch.com | 56.96 | 5.7825 |
| | | 22 | ABS Plastic (ATR Corrected) | NIST Library | 68.92 | 29.4314 |
| | | 37 | Aspirin Tablet (DRIFTS) | Aldrich Library | 68.93 | 0.1370 |
| 4 | 68.87 | 10 | Toluene (Transmission Cell) | FTIRSearch.com | 56.96 | 5.8218 |
| | | 14 | ABS Plastic (ATR - Ge Crystal) | User Library | 68.82 | 84.5645 |
| | | 3 | Polytetrafluoroethylene Film | C:\MyDocuments\reference | 68.87 | 30.4534 |
| 5 | 68.83 | 10 | Toluene (Transmission Cell) | FTIRSearch.com | 56.96 | 5.8254 |
| | | 14 | ABS Plastic (ATR - Ge Crystal) | User Library | 68.82 | 64.8435 |
| | | 37 | Aspirin Tablet (DRIFTS) | Aldrich Library | 68.83 | 0.1211 |

US 7,698,098 B2

EFFICIENT SPECTRAL MATCHING, PARTICULARLY FOR MULTICOMPONENT SPECTRA

FIELD OF THE INVENTION

This document concerns an invention relating generally to identification of unknown spectra obtained from spectrometer measurements, and more specifically to identification of unknown spectra via comparison of the unknown spectra to reference spectra.

BACKGROUND OF THE INVENTION

Figure 1:
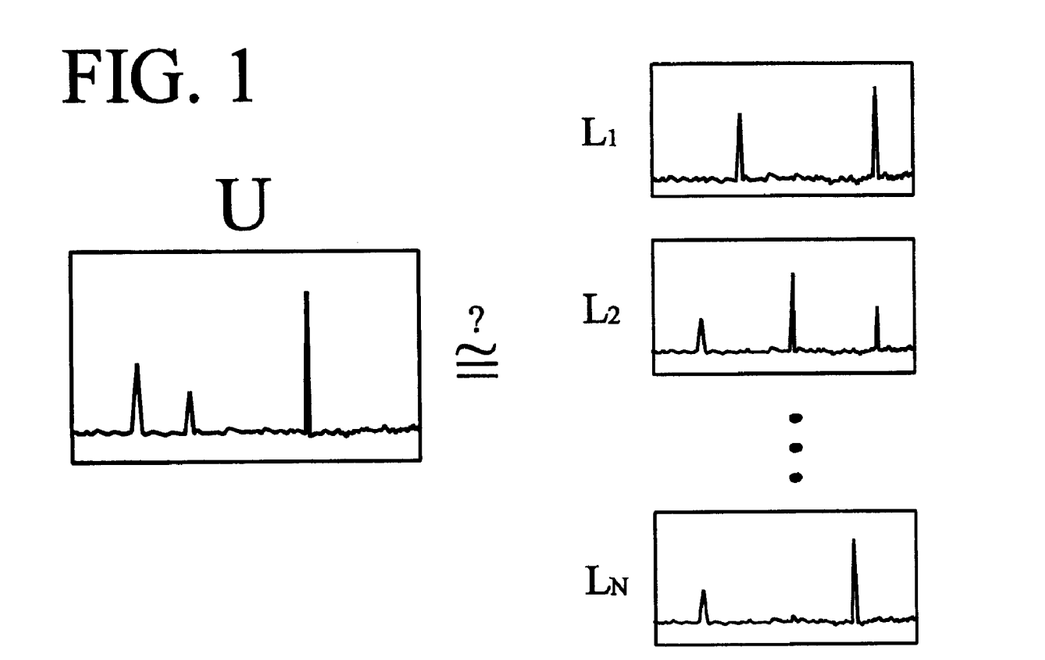
FIG. 1 is a schematic illustration depicting the problem of matching an unknown spectrum U to comparison spectra $L_1$, $L_2, \ldots L_N$ obtained from spectral libraries or other sources.

A molecular spectrometer (sometimes referred to as a spectroscope) is an instrument wherein a solid, liquid, or gaseous sample is illuminated, often with non-visible light such as light in the infrared region of the spectrum. The light from the sample is then captured and analyzed to reveal information about the characteristics of the sample. As an example, a sample may be illuminated with infrared light having known intensity across a range of wavelengths, and the light transmitted and/or reflected by the sample can then be captured for comparison to the illuminating light. Review of the captured spectra can then illustrate the wavelengths at which the illuminating light was absorbed by the sample. To illustrate, FIG. 1 illustrates an exemplary spectrum (denoted U) presented as a plot of light intensity versus light wavelength. The spectrum, and in particular the locations and amplitudes of the "peaks" therein, can be compared to libraries of previously-obtained reference spectra (denoted as $L_1$, $L_2, \ldots L_N$) to obtain information about the sample, such as its composition and characteristics. In essence, the spectrum serves as a "fingerprint" for the sample and for the substances therein, and by matching the fingerprint to one or more known fingerprints, the identity of the sample might be determined.

However, as when identifying a fingerprint, it can prove difficult and time-consuming to find a match for an unknown spectrum in a reference library. Even where an unknown spectrum is obtained from a sample having the same composition as the one from which a reference spectra was captured, an exact match is unlikely owing to differences in the measurement conditions between the unknown and reference spectra (e.g., differences in intensity/amplitude, differences in wavelength scaling/binning, different background noise levels, etc.). Further, while reference spectra are usually obtained from pure substances, unknown spectra often aren't. The unknown spectrum will therefore not match a single one of the reference spectra $L_1, L_2, \ldots L_N$, and will rather match a combination of two or more of these spectra. In such a combination, the spectra are effectively "overlaid" with each other, though each may have a different weight depending on the relative concentrations of the substances from which they originate. It should be appreciated that if one wishes to compare an unknown spectrum U to all possible combinations of one or more reference spectra $L_1, L_2, \ldots L_N$, this will typically be an exceedingly large number, particularly where a large reference library may have tens of thousands of entries (N being equal to the number of these entries). The computational time needed to perform these comparisons can be further magnified if quantitative analysis is to be performed as well as qualitative analysis, i.e., where the relative proportions of component spectra within the unknown spectrum are to be determined as well as their identities. Such quantitative analysis may require that regression be performed between a combination of reference spectra versus the unknown spectrum to determine the weighting that each reference spectrum should have to result in a combination which best matches the reference spectrum. As a result, exhaustive spectral matching can sometimes take hours—or even days—to perform, even where dedicated computers or other machines with high-speed processors are used.

SUMMARY OF THE INVENTION

The invention, which is defined by the claims set forth at the end of this document, is directed to methods and systems which can at least partially alleviate the aforementioned problems, and provide accurate spectral matches with fewer computations (and thus with greater speed). A basic understanding of some of the features of preferred versions of the invention can be attained from a review of the following brief summary of the invention, with more details being provided elsewhere in this document. To assist in the reader's understanding, the following review makes reference to the accompanying illustrations, which are briefly reviewed in the "Brief Description of the Drawings" section following this Summary section of this document.

Once an unknown spectrum is obtained from a spectrometer, a database, or another source, candidate spectra within the unknown spectrum can be identified in the following manner. Initially, comparison spectra—i.e., reference spectra for comparison—are accessed from one or more spectral libraries or other sources. The unknown spectrum is then compared to at least some of the comparison spectra to determine the degree to which the unknown spectrum corresponds to the comparison spectra. This step is schematically illustrated at 200 in FIG. 2, wherein the unknown spectrum U is compared to comparison spectra $L_1, L_2, \ldots L_N$. If the unknown spectrum U corresponds to a comparison spectrum to a desired degree—as by meeting or exceeding some user-defined or preset correspondence threshold—the comparison spectrum is regarded as being a candidate spectrum B(1). Thus, so long as the correspondence threshold is not set too high, several candidate spectra $B(\mathbf{1})_1, B(\mathbf{1})_2, \ldots B(\mathbf{1})_M$ will usually be identified. (If no candidate spectra are identified, the correspondence threshold can be set to a lower value.) Note that each candidate spectrum will represent a single component, i.e., a single reference spectrum obtained from a spectral library or other source (which generally represents the spectrum of a pure component/substance).

Figure 2:
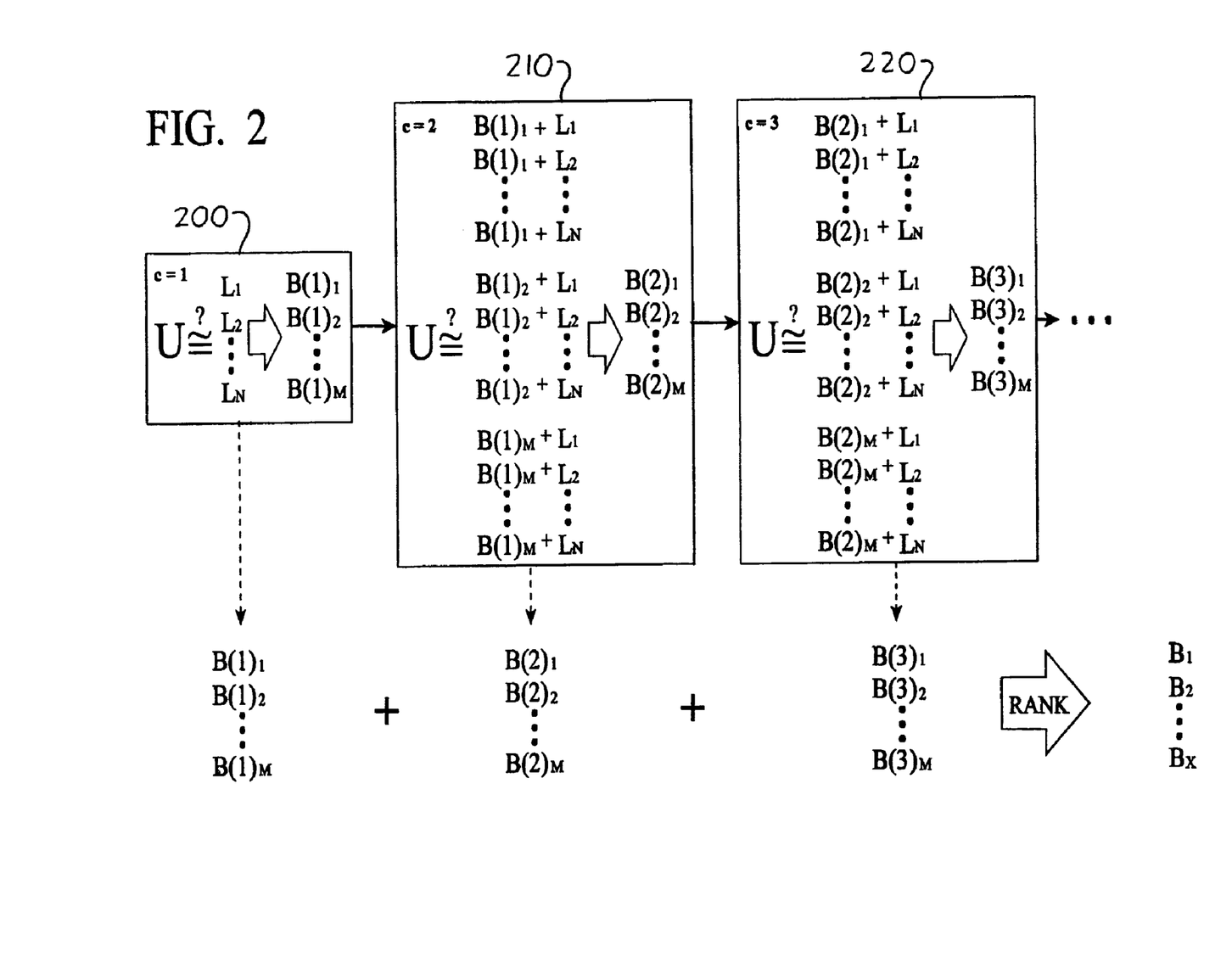
FIG. 2 is a schematic illustration depicting a preferred version of the matching methodology of the present invention.

Next, the possibility that the unknown spectrum might have arisen from a multi-component mixture is considered. New comparison spectra are generated, with each comparison spectrum being a combination of one of the previously identified candidate spectra and one of the comparison spectra from the spectral libraries or other sources. The unknown spectrum is then again compared to at least some of these new comparison spectra to determine the degree to which the unknown spectrum corresponds to the new comparison spectra. This step is schematically illustrated at 210 in FIG. 2, wherein the unknown spectrum U is compared to new comparison spectra:

$$B(\mathbf{1})_1 + L_1, B(\mathbf{1})_1 + L_2, \ldots B(\mathbf{1})_1 + L_N$$

(i.e., the first of the previously identified candidate spectra from 200 combined with each of the comparison spectra from the spectral libraries or other sources);

$$B(\mathbf{1})_2 + L_1, B(\mathbf{1})_2 + L_2, \ldots B(\mathbf{1})_2 + L_N$$

(i.e., the second of the previously identified candidate spectra from 200 combined with each of the comparison spectra from the spectral libraries or other sources); and so forth, until the unknown spectrum U is compared to new comparison spectra:

$$B(1)_M + L_1, B(1)_M + L_2, \ldots B(1)_M + L_N$$

(i.e., the last of the previously identified candidate spectra from 200 combined with each of the comparison spectra from the spectral libraries or other sources).

Where these comparisons find that one of the new comparison spectra has a desired degree of correspondence to the unknown spectrum U (as by meeting or exceeding the correspondence threshold), the new comparison spectrum is regarded to be a new candidate spectrum. These new candidate spectra are depicted in FIG. 2 at step 210 as $B(2)_1$, $B(2)_2, \ldots B(2)_M$. (It should be understood that if desired, M in step 210 need not be equal to M in step 200, i.e., the number of candidate spectra in step 210 need not be the same as the number of candidate spectra in step 200.) Here each candidate spectrum $B(2)_1, B(2)_2, \ldots B(2)_M$ represents two components, i.e., two combined reference spectra obtained from a spectral library or other source.

Figure 3:
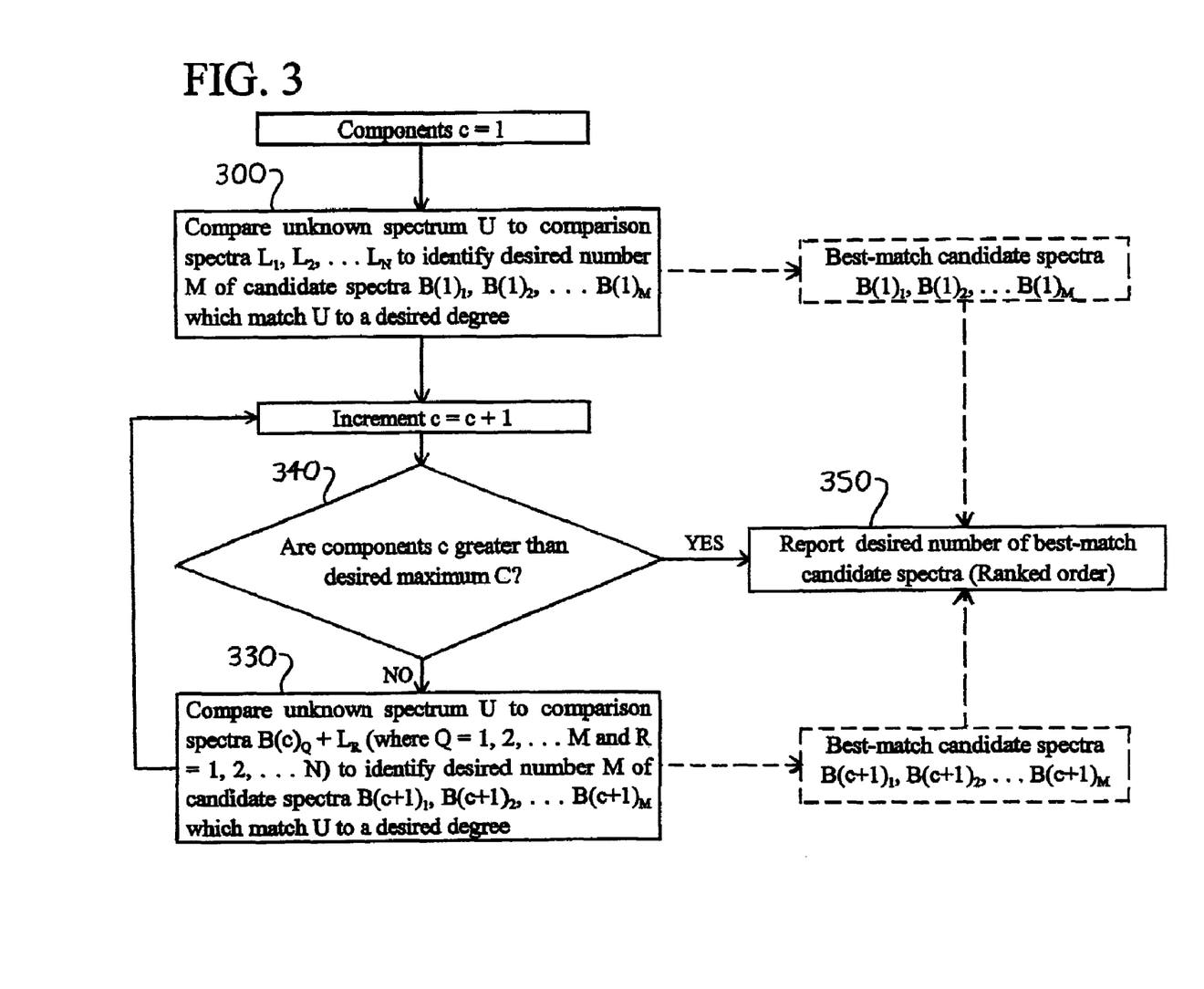
FIG. 3 is a flowchart depicting the matching methodology of FIG. 2, wherein box 300 is equivalent to step 200 of FIG. 2, box 330 is equivalent to steps 210 and 220 of FIG. 2 (as well as future repetitions of these steps), and the condition box 340 applies a stopping condition for reporting candidate spectra to a user (at box 350).

The foregoing step can then be repeated one or more times, with each repetition using the candidate spectra identified in the foregoing step to generate new comparison spectra. This is exemplified by step 220 in FIG. 2, wherein the candidate spectra $B(2)_1, B(2)_2, \ldots B(2)_M$ from step 210 are used in combination with the comparison spectra $L_1, L_2, \ldots L_N$ from the spectral libraries or other sources to generate new comparison spectra. Comparison of the unknown spectrum with these new comparison spectra in turn identifies new candidate spectra $B(3)_1, B(3)_2, \ldots B(3)_M$ (wherein M again need not be equal to M in steps 210 and/or 200). Repetition may cease when the candidate spectra include some desired number of components, e.g., once the new comparison spectra include a desired number of combined comparison/reference spectra obtained from a spectral library or other source. This condition is illustrated in the flowchart of FIG. 3, wherein box 300 is equivalent to step 200 of FIG. 2, box 330 is equivalent to steps 210 and 220 of FIG. 2 (as well as future repetitions of these steps), and the condition box 340 evaluates the number of components c in the candidate spectra and ceases repetition once some maximum number C is reached. Alternatively or additionally, repetition may cease when some desired number of candidate spectra are identified; when one or more candidate spectra are identified which match the unknown spectrum by at least some qualifying correspondence value (the qualifying correspondence value being greater than the threshold correspondence value), as discussed below; or when other suitable conditions arise.

Figure 4:
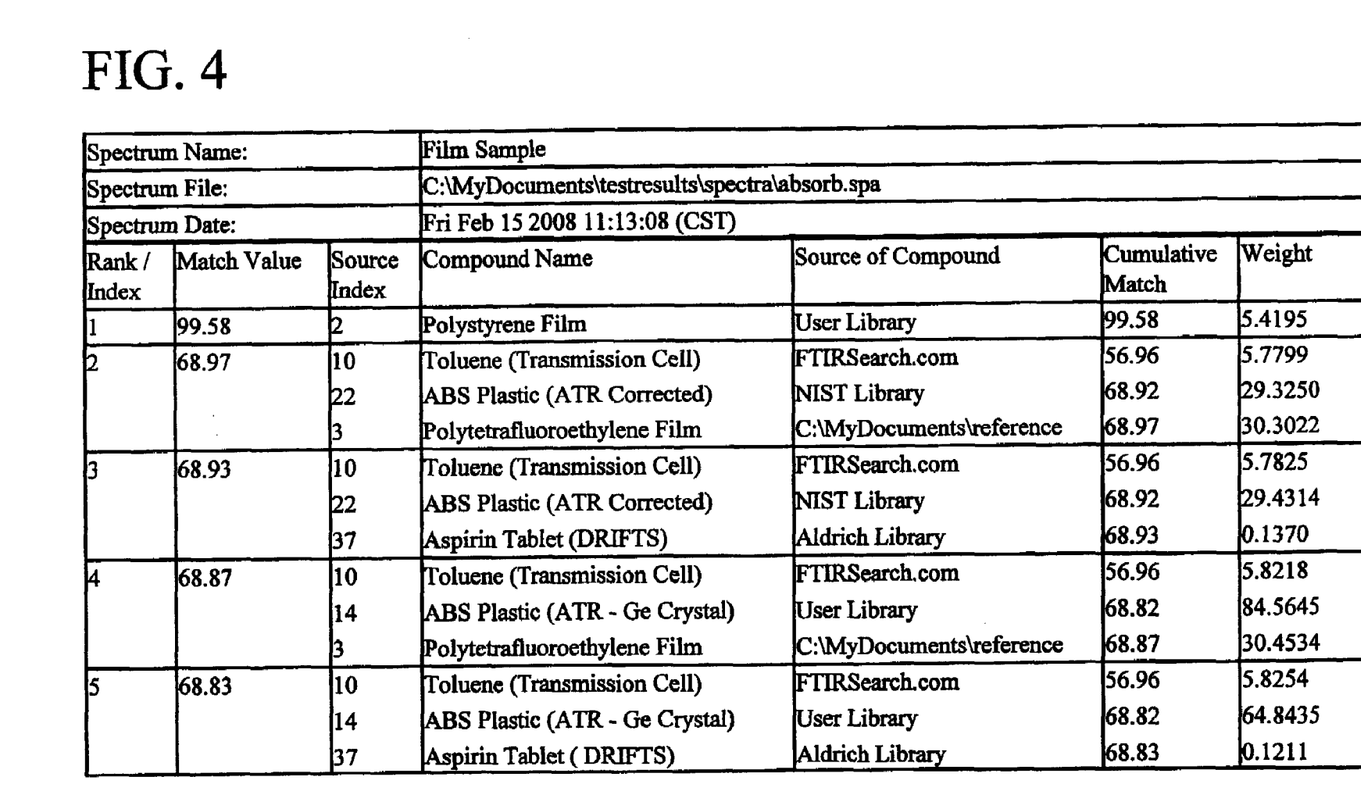
FIG. 4 depicts an exemplary output report of candidate spectra that might be presented to a user after the matching methodology is performed on the unknown spectrum.

At least some of the candidate spectra may then be presented to a user, with the candidate spectra preferably being presented to the user in ranked order such that those candidate spectra having greater correspondence to the unknown spectrum are presented first (as depicted at step 350 in FIG. 3). An exemplary format for an output list of candidate spectra that might be presented to a user is illustrated in FIG. 4. Here, details regarding the unknown spectrum are given in the heading of the output list, followed by details of the candidate spectra. The first listed candidate spectrum—listed with a rank/index of 1—is a spectrum for polystyrene film, and has a match metric (roughly equal to a "percentage of match") of 99.58 versus the unknown spectrum. The spectral library or other source of this candidate spectrum is also listed (here "User Example Library"), as is its location within the library/source (at "Source Index" no. 2, i.e., it is the second spectrum provided in the "User Example Library"). The second listed candidate spectrum is actually a combination of three spectra from spectral libraries or other sources—a Toluene (Transmission Cell) spectrum, an ABS Plastic (ATR Corrected) spectrum, and Polytetrafluouroethylene Film spectrum—wherein these spectra, when combined in appropriate proportions (as discussed below), yield a 68.97 match metric with the unknown spectrum. Their cumulative match metrics are also presented, with Toluene having a 56.96 match metric, Toluene and ABS together having a 68.92 match metric, and Toluene, ABS, and Polytetrafluouroethylene collectively yielding the 68.97 match metric. Again, the libraries or other sources of these spectra are provided along with an indication of the location of each spectrum within its library/source.

Additional metrics are also preferably provided with the output list, in particular, the weight of each comparison spectrum (each component/reference spectrum) within the candidate spectrum, i.e., the scaling factor used to adjust each comparison spectrum to obtain the best match with the unknown spectrum. For example, the first listed candidate spectrum (Polystyrene Film) has a weight of 5.4195, meaning that the unknown spectrum is estimated to have 5.4195 times the polystyrene content of the sample from which the candidate spectrum was obtained. The second listed candidate spectrum contains different weights of toluene, ABS, and polytetrafluouroethylene, with these weights being determined by regression analysis of the comparison spectra versus the unknown spectrum during the aforementioned comparison step (i.e., the various component/reference spectra within a comparison spectrum are proportioned to attain the best match to the unknown spectrum during comparison). Thus, the user may be provided with an at least approximate quantization of the components within the unknown spectrum.

The methodology above can be said to find "best-match" reference spectra, combine the best-match spectra to other reference spectra, and then identify further best-match spectra from these combinations (with the methodology iteratively continuing from the foregoing combination step). It is therefore seen that rather than comparing all possible combinations of reference spectra $L_1, L_2, \ldots L_N$, the methodology can consider far fewer combinations, basically by pruning out the reference spectra which have less similarity to the unknown spectrum. As a result, the methodology returns high-quality matches in far shorter time than in methods that consider all combinations, particularly where large numbers of reference spectra are used and where the unknown spectrum is reviewed for larger combinations of component/reference spectra—in some cases, returning results in minutes where hours were previously needed.

Further advantages, features, and versions of the invention are reviewed below, in conjunction with the accompanying drawings.

DETAILED DESCRIPTION OF PREFERRED VERSIONS OF THE INVENTION

Expanding on the discussion above, reference (comparison) spectra for use in the invention can be obtained from one or more spectral libraries or other sources. The spectral libraries used in the invention may be commonly available or proprietary libraries, and such libraries may each contain any number of reference spectra (i.e., the library may consist of a single reference spectrum, or conversely may include many thousands of reference spectra). Further, such reference spectra may be derived from actual measurements, from theory and mathematical computation, or from combinations of experimental and computational data.

Prior to performing the aforementioned comparisons between the unknown and comparison spectra, the invention may perform one or more transforms on one or both of the unknown and comparison spectra to expedite and/or increase the accuracy of the comparison process, or otherwise enhance data processing. As examples, the invention might perform one or more of data smoothing (noise reduction), peak discrimination, rescaling, domain transformation (e.g., transformation into vector format), differentiation, or other transforms on spectra. The comparison itself may also assume a variety of forms, as by simply comparing intensities/amplitudes across similar wavelength ranges between unknown and comparison spectra, by converting the unknown and comparison spectra into vectorial forms and comparing the vectors, or by other forms of comparison.

Additionally, the methodology described above can be modified to further expedite the identification of candidate spectra. As one example of such a modification, when generating a new comparison spectrum by combining a previously-identified candidate spectrum and a comparison spectrum obtained from a spectral library or other source, the combination might be skipped or discarded (i.e., deleted or not counted as a potential new candidate spectrum) if the candidate spectrum already contains the comparison spectrum. To more specifically illustrate, consider the situation where comparison spectrum $L_1$, which is obtained from a spectral library, is selected as $B(1)_1$ in step 200 (FIG. 2) owing to a sufficient match with unknown spectrum U. In the next iteration at step 210, the new comparison spectrum $B(1)_1+L_1$ can be skipped or discarded since it is equivalent to $L_1+L_1$ (i.e., reference spectrum $L_1$ combined with itself, which will merely again result in $L_1$). Thus, by avoiding the generation and/or use of comparison spectra which have redundant component spectra, the methodology can reserve computation time for comparison spectra which are more likely to yield new candidate spectra.

As another example of a modification that can be implemented to expedite the identification of candidate spectra, if a candidate spectrum matches the unknown spectrum by at degree greater than or equal to some "qualifying" correspondence value this qualifying correspondence value being greater than the threshold correspondence value—the comparison spectra therein (i.e., its component spectra) can be excluded from any later generation of new comparison spectra. In essence, this measure takes the approach that if a candidate spectrum is already a very good match for an unknown spectrum (e.g., if it has a qualifying correspondence value of above 95%), this may be sufficient, and there is no significant need to determine whether the match might be made even higher if the candidate spectrum was combined with other spectra.

Another modification that can be made to expedite the identification of candidate spectra applies in the special case where one or more of the components of the unknown spectrum are known—for example, when monitoring the output of a process which is intended to generate a material having known components in a predetermined quantity. In this case, during the first round of comparison (step 200 in FIG. 2, step 300 in FIG. 3), the candidate spectra $B(1)_1, B(1)_2, \ldots B(1)_M$ can simply be set to the spectra for the known components. Executing the remainder of the method will then serve to identify any additional components (i.e., impurities) that may be present, as well as the relative proportions of the various components.

It was previously noted that the correspondence threshold—i.e., the degree of match required between the unknown spectrum and a comparison spectrum for the comparison spectrum to be deemed a candidate spectrum—will yield no candidate spectra if set too high. Typically, a value of 90% correspondence is suitable for the correspondence threshold, though this value might be better set lower or higher depending on the details of the spectra under consideration. It is also possible to set the correspondence threshold to zero (or to a value near zero), in which case a candidate spectrum will result from each comparison spectrum. For example, if the correspondence threshold was set to zero in step 200 of FIGS. 2-3, M=N and $B(1)_1, B(1)_2, \ldots B(1)_M$ would each correspond to one of $L_1, L_2, \ldots L_N$. In this case, some of the candidate spectra will in reality be poor candidates because of poor matching with the unknown spectrum. It is then useful to rank the candidate spectra in order of highest correspondence to lowest correspondence, and then first consider those candidate spectra with highest correspondence when performing any subsequent steps. In this case, to reduce computations, it can be useful to discard the candidate spectra with lowest correspondence when performing any subsequent steps. For example, one might keep only the top 10%, 25% or 50% of the candidate spectra having highest correspondence, and to use these in subsequent steps.

It is expected that the invention will be implemented in spectral identification software for use in computers or other systems (e.g., spectrometers) which receive and analyze spectral data. Such systems may include portable/handheld computers, field measurement devices, application specific integrated circuits (ASICs) and/or programmable logic devices (PLD) provided in environmental, industrial, or other monitoring equipment, and any other systems wherein the invention might prove useful.

Additionally, while the invention has generally been described as being usable in the context of spectral matching for molecular spectrometers, it may alternatively or additionally be used in mass spectroscopy, X-ray spectroscopy, or other forms of spectroscopy. It might additionally be useful in other forms of measurement analysis wherein signals are measured versus reference values, in which case such signals and reference values may be regarded as "spectra" in the context of the invention.

It should be understood that the foregoing discussion merely relates to preferred versions of the invention, and the invention is not intended to be limited to these versions. Rather, the invention is only intended to be limited only by the claims set out below, with the invention encompassing all different versions that fall literally or equivalently within the scope of these claims.

What is claimed is:

1. A method of identifying candidate spectra within an unknown spectrum, the method including the steps of:
   a. obtaining a set of comparison spectra;
   b. comparing the unknown spectrum to the comparison spectra;
   c. identifying candidate spectra, each candidate spectrum being one of the comparison spectra having a desired degree of correspondence to the unknown spectrum;
   d. performing the following substeps one or more times:
      (1) generating new comparison spectra, each new comparison spectrum including:
         (a) one of the candidate spectra, and
         (b) one of the comparison spectra from the set;
      (2) comparing the unknown spectrum to the new comparison spectra;
      (3) identifying further candidate spectra, each candidate spectrum being one of the new comparison spectra having a desired degree of correspondence to the unknown spectrum,
      wherein, when performing substeps (1)-(3) again, the candidate spectra of substep (3) are used as the candidate spectra when generating new comparison spectra in substep (1).

2. The method of claim 1 further including the step of presenting a list of at least some of the candidate spectra.

3. The method of claim 2 wherein the candidate spectra within the list are presented in ranked order, with the candidate spectra having greater correspondence to the unknown spectrum being listed first.

4. The method of claim 1 wherein, prior to comparing the unknown spectrum to one of the comparison spectra, one or both of the unknown spectrum and the comparison spectrum are transformed.

5. The method of claim 1 wherein, when comparing the unknown spectrum to one of the comparison spectra, regression is performed on the comparison spectrum versus the unknown spectrum.

6. The method of claim 5 wherein:
   a. when performing regression on the comparison spectrum, a regression weight is calculated; and
   b. the comparison spectrum is weighted by its regression weight.

7. The method of claim 6:
   a. further including the step of presenting a list of at least some of the candidate spectra, and
   b. wherein the regression weights of the comparison spectra defining the candidate spectra are presented in the list.

8. The method of claim 1 wherein, when generating new comparison spectra, each comparison spectrum includes:
   a. one of the candidate spectra, and
   b. one of the comparison spectra, wherein this comparison spectrum is not already included within the candidate spectrum.

9. The method of claim 1 wherein if any candidate spectrum contains the same comparison spectra as a previously-identified candidate spectrum, one of the candidate spectrum and the previously-identified candidate spectrum is discarded.

10. The method of claim 1 wherein, if a candidate spectrum corresponds to the unknown spectrum by at degree greater than or equal to a qualifying correspondence value, the comparison spectra therein are excluded from any later generation of new comparison spectra.

11. The method of claim 1 wherein step d. is halted once the new comparison spectra include a desired number of comparison spectra.

12. A method of identifying candidate spectra within an unknown spectrum, the method including the steps of:
   a. providing one or more candidate spectra, each candidate spectrum being assumed to represent at least a portion of the unknown spectrum;
   b. performing the following substeps one or more times:
      (1) generating comparison spectra, each comparison spectrum being a combination of:
         (a) one of the candidate spectra, and
         (b) a reference spectrum corresponding to an identified substance,
         wherein each candidate spectrum is combined with several different reference spectra to generate several comparison spectra;
      (2) comparing the unknown spectrum to the comparison spectra;
      (3) identifying further candidate spectra, each candidate spectrum being one of the comparison spectra which at least partially matches the unknown spectrum,
      wherein, when performing the foregoing substeps (1)-(3) again, the candidate spectra of substep (3) are used as the candidate spectra when generating comparison spectra in substep (1).

13. The method of claim 12 wherein the step of providing one or more candidate spectra includes:
   a. obtaining a set of several different reference spectra, each corresponding to an identified substance;
   b. comparing the unknown spectrum to the reference spectra;
   c. identifying the candidate spectra, each candidate spectrum being one of the reference spectra which at least partially matches the unknown spectrum.

14. The method of claim 12 further including the step of presenting a list of at least some of the candidate spectra, wherein the candidate spectra within the list are presented in ranked order with the candidate spectra having higher matching to the unknown spectrum being listed first.

15. The method of claim 12 further including the step of performing a transform on at least one of:
   a. the unknown spectrum;
   b. at least one of the comparison spectra;
   c. at least one of the reference spectra; and
   d. at least one of the candidate spectra.

16. The method of claim 12 further including the step of performing regression on at least one of the comparison spectra versus the unknown spectrum.

17. A method of identifying candidate spectra within an unknown spectrum, the method including the steps of:
   a. comparing the unknown spectrum to at least some comparison spectra, each comparison spectrum being obtained from a spectral library;
   b. saving at least some of the comparison spectra that best match the unknown spectrum, each such comparison spectrum being a candidate spectrum;
   c. creating new comparison spectra, each new comparison spectrum being a combination of:
      (1) one of the candidate spectra, and
      (2) one of the comparison spectra within the spectral library,
   d. comparing the unknown spectrum to at least some of the new comparison spectra,
   e. saving at least some of the new comparison spectra that best match the unknown spectrum, each such comparison spectrum being a candidate spectrum;

f. repeating the foregoing step c. onward at least once;

g. presenting at least some of the candidate spectra.

18. The method of claim 17 wherein steps c.-f. are halted once the new comparison spectra include a predefined number of comparison spectra.

19. The method of claim 17 wherein the candidate spectra are presented in ranked order, with the candidate spectra having greater correspondence to the unknown spectrum being presented first.

20. The method of claim 17 wherein at least one of the following substeps is performed when comparing the unknown spectrum to one of the comparison spectra:

a. transforming one or both of the unknown spectrum and the comparison spectrum; and b. regressing the comparison spectrum versus the unknown spectrum.

21. A system for identifying candidate spectra within an unknown spectrum, the system including a computer which:

a. receives an unknown spectrum;

b. accesses one or more records, each record including one or more comparison spectra;

c. compares the unknown spectrum to at least some of the comparison spectra from the records;

d. identifies candidate spectra, each candidate spectrum being one of the comparison spectra which matches the unknown spectrum with a desired degree of correspondence;

e. compares the unknown spectrum to new comparison spectra, each new comparison spectrum being a combination of:

(1) one of the candidate spectra, and (2) one of the comparison spectra from the records, f. identifies new candidate spectra, each new candidate spectrum being one of the new comparison spectra which matches the unknown spectrum with a desired degree of correspondence;

g. presents at least some of the candidate spectra to a user.

22. The system of claim 21 wherein the system, after identifying new candidate spectra:

a. compares the unknown spectrum to new comparison spectra, each new comparison spectrum being a combination of:

(1) one of the new candidate spectra, and (2) one of the comparison spectra from the records, b. identifies further new candidate spectra, wherein each new candidate spectrum is one of the new comparison spectra which matches the unknown spectrum with a desired degree of correspondence.

23. The system of claim 21 wherein the candidate spectra are presented to the user in ranked order, with the candidate spectra having the highest degree of correspondence to the unknown spectrum being presented first.

24. The system of claim 21 wherein the computer transforms at least one of:

a. the unknown spectrum, and b. the comparison spectrum, prior to comparing them.

25. The system of claim 21 wherein the computer performs regression on the comparison spectrum versus the unknown spectrum when comparing them.

\* \* \* \* \*

UNITED STATES PATENT AND TRADEMARK OFFICE
CERTIFICATE OF CORRECTION

PATENT NO. : 7,698,098 B2  Page 1 of 1
APPLICATION NO. : 12/032794
DATED : April 13, 2010
INVENTOR(S) : Garry L. Ritter et al.

It is certified that error appears in the above-identified patent and that said Letters Patent is hereby corrected as shown below:

Title page, item (75) Inventors:
replace "Gary L. Ritter"
with --Garry L. Ritter--

Signed and Sealed this

Twenty-ninth Day of June, 2010

David J. Kappos
*Director of the United States Patent and Trademark Office*